(12) United States Patent
Joshi-Hangal et al.

(10) Patent No.: US 6,710,195 B2
(45) Date of Patent: Mar. 23, 2004

(54) METHOD FOR PREPARING AND USING POLYOXYETHYLATED CASTOR OIL IN PHARMACEUTICAL COMPOSITIONS

(75) Inventors: Rajashree Joshi-Hangal, Union City, CA (US); Joseph Rubinfeld, Danville, CA (US); Sanjeev Redkar, Union City, CA (US); Ashok Y. Gore, San Ramon, CA (US)

(73) Assignee: SuperGen, Inc., Dublin, CA (US)

( * ) Notice: Subject to any disclaimer, the term of this patent is extended or adjusted under 35 U.S.C. 154(b) by 0 days.

(21) Appl. No.: 10/306,824

(22) Filed: Nov. 26, 2002

(65) Prior Publication Data

US 2003/0153614 A1 Aug. 14, 2003

Related U.S. Application Data

(60) Provisional application No. 60/333,459, filed on Nov. 26, 2001.

(51) Int. Cl.[7] ............................................... C07C 51/16
(52) U.S. Cl. ....................................... 554/132; 514/449
(58) Field of Search ......................... 554/132; 514/449

(56) References Cited

U.S. PATENT DOCUMENTS 5,504,102 A * 4/1996 Agharkar et al. ............ 514/449
6,071,952 A * 6/2000 Owens et al. ................ 514/449

* cited by examiner

Primary Examiner—Deborah D. Carr
(74) Attorney, Agent, or Firm—Shirley Chen; Wilson Sonsini; Goodrich & Rosati

(57) ABSTRACT

A method is provided for preparing a pharmaceutical composition comprising: taking polyoxyethylated castor oil which if diluted 1:10 in water has a pH greater than 5 and aging the polyoxyethylated castor oil by exposing the polyoxyethylated castor oil to a gas comprising oxygen for a period of time, the exposure to the gas over the period of time causing an acidity of the polyoxyethylated castor oil to increase; and forming a pharmaceutical composition comprising the aged polyoxyethylated castor oil and a pharmaceutically active agent such as paclitaxel; wherein at least 80% of the potency of the pharmaceutically active agent is retained by the pharmaceutical composition after the pharmaceutical composition is stored for at least 7 days at 40° C.

70 Claims, 3 Drawing Sheets

METHOD FOR PREPARING AND USING POLYOXYETHYLATED CASTOR OIL IN PHARMACEUTICAL COMPOSITIONS

CROSS REFERENCE TO RELATED APPLICATION

This application claims the benefit of U.S. Provisional Application No. 60/333,459, filed Nov. 26, 2001, entitled "Method For Preparing And Using Polyoxyethylated Castor Oil In Pharmaceutical Compositions." This application is incorporated herein by reference.

BACKGROUND OF THE INVENTION

1. Field of the Invention

The present invention relates generally to the formulation of pharmaceutical compositions. More particularly, the invention relates to the preparation and use of polyoxyethylated castor oil in pharmaceutical compositions.

2. Description of Related Art

Paclitaxel has proven to be a highly sucessful antineoplastic agent. It is currently administered to patients in a formulation that comprises paclitaxel, Cremophor® (polyoxyethylated castor oil), and ethanol.

Paclitaxel is a unique diterpene derived from the bark of the *Taxus brevifolia* (Pacific yew) tree. A crude extract of the bark demonstrated antineoplastic activity in preclinical tumor screening 30 years ago as part of the National Cancer Institute's (NCI's) large-scale screening program. The active component of the extract, paclitaxel, was isolated and described by M. C. Wani et al, Plant antitumor agents. VI: The isolation and structure of Paclitaxel. a novel antileukemic and antitumor agent from *Taxus brevifolia,* J. Am. Chem. Soc. 93:2325–2327 (1971). This document, and all others referred to herein, are incorporated by reference as if reproduced fully below.

Unfortunately, paclitaxel is poorly soluble in water (less than 0.01 mg/mL) and other common vehicles used for the parenteral administration of drugs. Certain organic solvents, however, may at least partially dissolve paclitaxel. However, when a water-miscible organic solvent containing paclitaxel at near its saturation solubility is diluted with aqueous infusion fluid, the drug may precipitate.

Solubilization of paclitaxel with surfactants allows for dilution of saturated or near-saturated formulations of paclitaxel. Specifically, paclitaxel has been formulated using 50% Cremophor® EL 50% dehydrated alcohol (USP, United States Pharmacopoeia), diluted in NS normal saline or D5W (5% dextrose in water) to a final concentration of 5% Cremophor® EL and 5% dehydrated alcohol or less, for the intravenous administration of the drug to humans in early clinical trials. (Cremophor® EL; Badische Anilin und Soda Fabrik AG (BASF), Ludwigshafen, Federal Republic of Germany). A concentrate of paclitaxel for injection is currently available from Bristol-Myers Squibb Co. (New York, N.Y.) in vials where each milliliter of formulation contains approximately 6 mg Paclitaxel, 527 mg of Cremophor® EL, and 49.7% (vol/vol) dehydrated alcohol. This concentrated formulation must be further diluted with NS, D5W, D5NS (normal saline, 5% dextrose in water and 5% dextrose in normal saline) or D5W-R (Ringer's solution with 5% dextrose in water) prior to administration. It has been noted that the Cremophor®/ethanol formulation of paclitaxel precipitates upon dilution with infusion fluid, and fibrous precipitates formed in some compositions during storage for extended periods of time. Additional information regarding Cremophor® formulations of paclitaxel may be found in Agharkar et al., U.S. Pat. No. 5,504,102.

It was discovered that commercial grade Cremophor® EL with ethanol as a co-solvent, although effective in solubilizing pharmaceutical agents, produces injection compositions that exhibit instability over extended periods of time. In particular, concentrated formulations of paclitaxel in a co-solvent of 50:50 by volume of dehydrated ethyl alcohol and commercial grade Cremophor® EL exhibit a loss of potency of greater than 60% after storage for 12 weeks at 50° C. The loss of potency is attributed to the decomposition of paclitaxel during storage.

Various methods of stabilizing paclitaxel solubilized in polyoxyethylated castor oil and ethanol during storage have been developed. For example, U.S. Pat. Nos. 5,504,102, 5,733,888, 5,972,992, 5,977,164, 6,071,952, 6,140,359 each teach adding an agent to modify the pH of the concentrated formulation in order to stabilize paclitaxel.

Other concentrated formulations of taxoid compounds have been developed. For example, several U.S. patents assigned to Rhone-Poulenc Rorer (U.S. Pat. Nos. 5,403,858, 5,438,072, 5,670,536, 5,698,582, 5,714,512) provide a formulation composed of a taxane compound dissolved in a surfactant selected from a group consisting of polysorbate, polyoxyethylene glycol, or hydrogenated castor oil, and essentially free of ethanol.

U.S. Pat. No. 6,071,952 to Owens et al discloses a human administration comprising an anti-neoplastic taxol compound, a solubilizing/dispersing agent, and a stabilizing amount of an anti-oxidant.

It is important for concentrated formulations of paclitaxel to have prolonged shelf lives since product instability increases manufacturing costs due to extensive consumption of raw materials and yields a product of inferior quality, both translating into higher patient cost. Additional stabilization strategies for paclitaxel and other pharmaceutically active agents are therefore needed, one of which is provided by the present invention.

SUMMARY OF THE INVENTION

The present invention provides novel methods of preparing pharmaceutical formulations containing polyoxyethylated castor oil as excipient. In particular, methods are provided for preparing pharmaceutical compositions containing paclitaxel formulated with polyoxyethylated castor oil that has been aged to a reduced pH value relative to that of polyoxyethylated castor oil freshly synthesized. Aging can be performed by varying the time and condition of storage, such as by heating, pressurization, air-sparging or combinations thereof, without substantially changing physical and chemical characteristics of polyoxyethylated castor oil except its pH value. Such aged polyoxyethylated castor oil is then mixed with a pharmaceutically active agent such as paclitaxel. Pharmaceutical compositions comprising the aged polyoxyethylated castor oil and a pharmaceutically active agent are also provided. Paclitaxel formulations containing the aged polyoxyethylated castor oil that is acidified without addition of an acidifying chemical are believed to be physically and chemically more stable than those formulated with polyoxyethylated castor oil freshly synthesized or at higher pH.

In one aspect of the invention, a method is provided for preparing a pharmaceutical composition.

In one embodiment, the method comprises:

taking polyoxyethylated castor oil which if diluted 1:10 in water has a pH greater than 6 and aging the polyoxyethylated castor oil by exposing the polyoxyethylated castor oil to a gas comprising oxygen for a period of time, the exposure to the gas over the period of time causing an acidity of the polyoxyethylated castor oil to increase; and forming a pharmaceutical composition comprising the aged polyoxyethylated castor oil and a pharmaceutically active agent such as paclitaxel and docetaxel, wherein at least 80% of the potency of the pharmaceutically active agent is retained by the pharmaceutical composition after the pharmaceutical composition is stored for at least 7 days at 40° C.

In another embodiment, the method comprises:

taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and forming a pharmaceutical composition comprising the aged polyoxyethylated castor oil and a pharmaceutically active agent such as paclitaxel and docetaxel.

Optionally, aging the polyoxyethylated castor oil is performed until the aged polyoxyethylated castor oil, if diluted 1:10 in water, has a pH equal to or lower than 5.5, optionally equal to or lower than 5, optionally equal to or lower than 4.8.

Optionally, aging the polyoxyethylated castor oil is performed until the aged polyoxyethylated castor oil, if diluted 1:10 in water, has a pH between 3.7 and 5.9, optionally between 3.8 and 5.5, optionally between 3.9 and 5, and optionally between 4 and 4.8.

In yet another embodiment, the method comprises:

taking polyoxyethylated castor oil which if diluted 1:10 in water has a pH greater than 6 and aging the polyoxyethylated castor oil by exposing the polyoxyethylated castor oil to a gas comprising oxygen for a period of time, the exposure to the gas over the period of time causing an acidity of the polyoxyethylated castor oil to increase; and forming a pharmaceutical composition comprising the aged polyoxyethylated castor oil, ethanol and paclitaxel; wherein at least 80% of the paclitaxel potency is retained by the pharmaceutical composition after the pharmaceutical composition is stored for at least 7 days at 40° C.

In yet another embodiment, the method comprises:

taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and forming a pharmaceutical composition comprising the aged polyoxyethylated castor oil, ethanol and paclitaxel; wherein at least 80% of the paclitaxel potency is retained by the pharmaceutical composition after the pharmaceutical composition is stored for at least 7 days at 40° C.

In yet another embodiment, the method comprises:

taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and forming a pharmaceutical composition comprising the aged polyoxyethylated castor oil, ethanol and paclitaxel, wherein at least 80% of the paclitaxel potency is retained by the pharmaceutical composition after the pharmaceutical composition is stored for at least 7 days at 40° C.

Optionally, aging the polyoxyethylated castor oil is performed until the aged polyoxyethylated castor oil, if diluted 1:10 in water, has a pH less than or equal to 4.7, optionally equal to or lower than 4.5, optionally equal to or lower than 4.2.

Optionally, aging the polyoxyethylated castor oil is performed until the aged polyoxyethylated castor oil, if diluted 1:10 in water, has a pH between 3.7 and 4.9, optionally between 3.8 and 4.5, optionally between 3.9 and 4.3, and optionally between 4.0 and 4.5.

According to any of the above methods, the pharmaceutical composition optionally comprises 500–550 mg/mL of polyoxyethylated castor oil, and 40–60% of ethanol vol/vol. Optionally, the pharmaceutical composition comprises 527 mg/mL of polyoxyethylated castor oil, and 49.7% of ethanol vol/vol.

In regard to any of the above methods, an antioxidant or a pharmaceutically acceptable alcohol such as ethanol may optionally be added to the aged polyoxyethylated castor oil or the pharmaceutical composition.

Aging of the polyoxyethylated castor oil may be performed over a variety of time periods and under various conditions before mixing the aged polyoxyethylated castor oil with the pharmaceutically active agent such as paclitaxel.

In one variation, aging the polyoxyethylated castor oil is performed for at least 30 minutes at a temperature range between 0° C. and 70° C. Preferably, aging the polyoxyethylated castor oil is performed for at least 3 day, optionally for at least 7 days, and optionally for at least 14 days, at a temperature range between 30° C. and 70° C., optionally between 40° C. and 60° C., and optionally between 45° C. and 55° C. As demonstrated in the present invention, acidification of polyoxyethylated castor oil is significantly accelerated by aging at a temperature higher than the ambient temperature (about 20–25° C.) and/or by sparging air into the polyoxyethylated castor oil.

In another variation, aging the polyoxyethylated castor oil is performed for at least 30 minutes at a temperature range between 0° C. and 70° C. by sparging the polyoxyethylated castor oil with air.

In yet another variation, aging the polyoxyethylated castor oil is performed for at least 30 minutes at a temperature range between 0° C. and 70° C. by pressurizing the polyoxyethylated castor oil to be at least 1.2 atmospheric pressure, optionally at least 1.5 atmospheric pressure, optionally at least 2.0 atmospheric pressure, and optionally at least 3.0 atmospheric pressure.

In regard to any of the above methods, optionally, at least 80%, at least 90% or at least 95% of the potency of paclitaxel is retained by the pharmaceutical composition after the pharmaceutical composition is stored for at least 7 days at 40° C.

Also in regard to any of the above methods, it is preferred that no agent is added that functions to increase the acidity of the polyoxyethylated castor oil. However, a chemical acidifying agent may optionally be added to the polyoxyethylated castor oil before, during or after the aging process to further increase the acidity of the polyoxyethylated castor oil. The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

In another aspect of the invention, a pharmaceutical composition is provided.

In one embodiment, the pharmaceutical composition comprises: polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and a pharmaceutically active agent such as paclitaxel; wherein the pharmaceutical composition does not comprise an agent added to the polyoxyethylated castor oil that functions to increase the acidity of the polyoxyethylated castor oil.

In another embodiment, the pharmaceutical composition comprises: polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and a pharmaceutically active agent such as paclitaxel; wherein at least 80% of the potency of the pharmaceutically active agent is retained by the pharmaceutical composition after the pharmaceutical composition is stored for at least 7 days at 40° C.

In yet another embodiment, the pharmaceutical composition comprises: polyoxyethylated castor oil that has been modified by taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and a pharmaceutically active agent such as paclitaxel; wherein at least 80% of the potency of the pharmaceutically active agent is retained by the pharmaceutical composition after the pharmaceutical composition is stored for at least 7 days at 40° C.

In yet another aspect of the invention, a pharmaceutical is provided.

In one embodiment, the pharmaceutical comprises: a sealed vial comprising polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and a pharmaceutically active agent such as paclitaxel, wherein the pharmaceutical does not comprise an agent added to the polyoxyethylated castor oil that functions to increase the acidity of the polyoxyethylated castor oil.

In another embodiment, the pharmaceutical comprises: a sealed vial comprising polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and a pharmaceutically active agent such as paclitaxel, wherein at least 80% of the potency of the pharmaceutically active agent is retained by the pharmaceutical after the pharmaceutical is stored for at least 7 days at 40° C.

In yet another embodiment, the pharmaceutical comprises: a sealed vial comprising polyoxyethylated castor oil that has been modified by taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and a pharmaceutically active agent such as paclitaxel, wherein at least 80% of the potency of the pharmaceutically active agent is retained by the pharmaceutical after the pharmaceutical is stored for at least 7 days at 40° C.

In regard to any embodiment of the above pharmaceutical compositions or pharmaceuticals, an antioxidant or a pharmaceutically acceptable alcohol such as ethanol may optionally be added to the aged polyoxyethylated castor oil or the pharmaceutical composition. For example, the pharmaceutical composition or pharmaceutical may comprise 500–550 mg/mL of polyoxyethylated castor oil, and 40–60% of ethanol vol/vol and optionally comprises 527 mg/mL of polyoxyethylated castor oil, and 49.7% of ethanol vol/vol.

In regard to any embodiment of the above pharmaceutical compositions or pharmaceuticals, a pharmaceutically acceptable glycol such as propylene glycol and polyethylene glycol (PEG) or amide such as 2-pyrrolidone, N-methylpyrrolidone and N,N-dimethyl acetamide may optionally be added to the aged polyoxyethylated castor oil or the pharmaceutical composition.

In regard to any embodiment of the above pharmaceutical compositions or pharmaceuticals, the concentration of paclitaxel in the pharmaceutical composition is optionally about 1–20 mg/g, optionally about 3–15 mg/g, and optionally about 5–8 mg/g.

In regard to any embodiment of the above pharmaceutical compositions or pharmaceuticals, optionally at least 80%, at least 90% or at least 95% of the potency is retained by the pharmaceutical composition after the pharmaceutical composition is stored for at least 7 days at 40° C.

Also in regard to any embodiment of the above pharmaceutical compositions or pharmaceuticals, preferably no acidifying chemical agent is added that functions to increase the acidity of the polyoxyethylated castor oil. However, an inorganic or organic acid may be added to the polyoxyethylated castor oil before, during or after the aging process to further reduce the pH of the polyoxyethylated castor oil.

BRIEF DESCRIPTION OF FIGURES

The various features and aspects of the instant invention may be more readily understood, in conjunction with the description to follow, by reference to the following drawings.

DEFINITIONS

Figure 1:
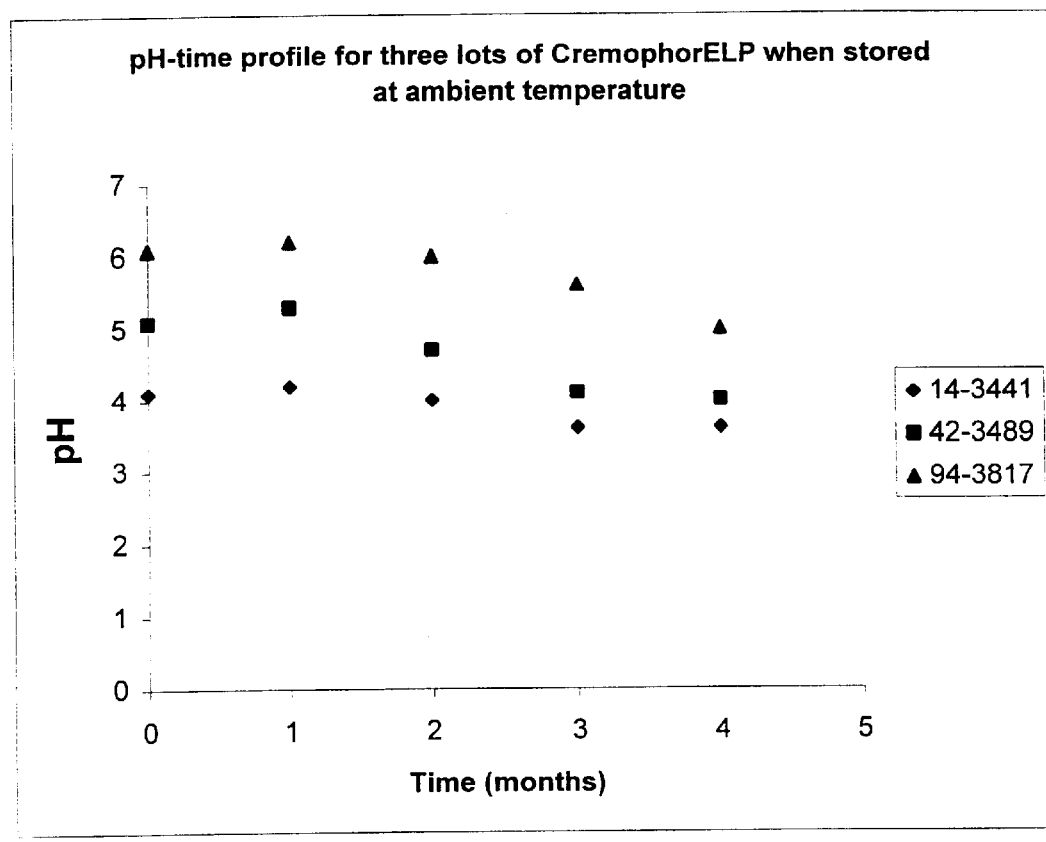
FIG. 1 is a plot over time of the pH of samples of Cremophor® ELP (after having been diluted 1/10(vol/vol) with $H_2O$) that have been stored under ambient conditions.

The term "polyoxyethylated castor oil" (also sometimes referred to elsewhere as polyethoxylated castor oil) refers to products resulting from the condensation of castor oil with ethylene oxide. Polyoxyethylated castor oil is commercially available and has been used to solubilize and disperse anti-neoplastic compounds such as paclitaxel. For example, polyoxyethylated castor oil products are available under the trade names Cremophor® EL and Cremophor® ELP. These products are readily available through BASF Germany. The preparation of Cremophor® EL is described in U.S. Pat. No. 3,070,499. A low cation version of polyoxyethylated castor oil, Cremophor® EL and its preparation is described in U.S. Pat. No. 5,925,776.

The term "paclitaxel" is intended to include paclitaxel, taxoid, taxane, or any derivatives and analogs of paclitaxel, such as the semi-synthetic drug derived from precursor extracted from the needles of the European yew tree *Taxus baccata*, docetaxel or Taxotere®.

The term "therapeutic" refers to prophylaxis and to amelioration and cure of a disease or pathology, and/or the symptoms and/or sequelae thereof. Therapeutic agents may exert their effects, for example, by preventing or halting the pathogenesis, reducing the rate or extent of pathophysiologic progression, or alleviating the symptomatology of a disease or pathologic condition.

The phrase "therapeutically acceptable" in the context of a describing a pharmacologic or pharmaceutical composition, encompasses the concept of therapeutic index of a dosing unit as commonly defined in terms of a ratio of $LD_{50}$ (lethal dose to 50% of population) to $ED_{50}$ (effective dose to 50% of population) in the context of the severity of a disease process as described, for example in Hardman & Limbird, Eds., *Goodman & Gilman's Pharmacologic Basis of Therapeutics*, $10^{th}$ Ed, McGraw-Hill Co., Inc. (2001).

Additionally encompassed by therapeutic acceptability are concepts of long term or cumulative toxicity, as for example when a composition or impurity thereof can cause pathology over a long period of administration without there being a lethal dose for acute administration. Also encompassed infectious pathogenic impurities, including eukaryotic, prokaryotic, viral and proteinacious infectious agents.

The population is typically a human population, but therapeutically acceptable for humans ipso facto encompasses therapeutic acceptability for other members of Kingdom animalia. Thus any factor that affects efficacy and/or acute or long-term toxicity of a dosing unit is encompassed by the phrase therapeutically acceptable. Therapeutically acceptable incorporates suitability for administration in terms of acceptable toxicity for the disease process treated. A therapeutically acceptable formulation must have both acceptable efficacy and acute and chronic toxicity. In the case of a pharmacologic agent that decomposes into a biologically or pharmacologically inactive decomposition product that is relatively non-toxic compared to the pharmacologic agent, therapeutic acceptability is in terms of an acceptable level of the active agent.

The term "pH" refers to or describes a measurement made of the $-\log_{10}$ of $[H^+]$ (concentration in units M=moles/liter) of a solution. Because pH measurements are preferably made in an aqueous environment and polyoxyethylated castor oil is anhydrous, polyoxyethylated castor oil is diluted 1:10 using deionized or distilled water prior to measuring its pH. For example, a sample volume, V, of polyoxyethylated castor oil is taken and diluted in a volume, $10*V$, of water prior. After dilution, the pH of the resulting solution is measured.

DETAILED DESCRIPTION OF THE INVENTION

The present invention is directed to pharmaceutical compositions that comprise polyoxyethylated castor oil that have been aged by exposing the polyoxyethylated castor oil to a gas comprising oxygen for a period of time, the exposure to the gas over the period of time causes an acidity of the polyoxyethylated castor oil to increase. The present invention is also related to methods for aging polyoxyethylated castor oil and for preparing these pharmaceutical compositions.

The present invention arises from the inventors' discovery that exposing polyoxyethylated castor oil to a gas comprising oxygen causes the acidity of the polyoxyethylated castor oil to increase. This discovery is evidenced by the observation that the pH of 1:10 water diluted solutions made from samples of polyoxyethylated castor oil aged for different periods of time decrease as a function of time.

U.S. Pat. Nos. 5,504,102, 5,733,888, 5,972,992, 5,977,164, 6,071,952, 6,140,359 teach that extraneous acidifying agents need to be added to paclitaxel—polyoxyethylated castor oil—ethanol formulations in order to stabilize the paclitaxel. By aging the polyoxyethylated castor oil by exposing it to oxygen, the polyoxyethylated castor oil is acidified without having to add an acidifying agent to the polyoxyethylated castor oil.

The acidification of the polyoxyethylated castor oil achieved by aging the polyoxyethylated castor oil according to the present invention is believed to provide several advantages over acidifying the polyoxyethylated castor oil by the addition of an acidifying agent, such as mineral acid. For example, titration with an acidifying agent may be imprecise. Furthermore, when the native acidity of the polyoxyethylated castor oil changes via aging according to the present invention, it is likely to be as a result of the formation of carboxylic acids. This higher concentration of carboxylic acids serves as a more stable buffer for the protonation of the paclitaxel molecules that impedes paclitaxel's decomposition.

While the present invention is largely described herein in relation to pharmaceutical compositions comprising paclitaxel, it is noted that the invention is intended to encompass any pharmaceutical compositions comprising a pharmaceutically active agent in combination with polyoxyethylated castor oil aged according to the present invention. Numerous different pharmaceutically active agents may be formulated with polyoxyethylated castor oil. For example, U.S. Pat. No. 5,504,102 to Agharkar, et al. teaches formulating paclitaxel, teniposide, camptothecin and other antineoplastic agents with polyoxyethylated castor oil.

In one embodiment, the pharmaceutical composition comprises a taxane or analog or derivative of a taxane as the pharmaceutically active agent such as docetaxel. In a particular embodiment, the taxane is paclitaxel. Given the success of paclitaxel as an antineoplastic agent, a great deal of research has been performed to identify pharmaceutically active taxanes as well as analogs and derivatives of taxanes, all of which may be formulated with polyoxyethylated castor oil aged according to the present invention.

Given the significance of paclitaxel, a particular embodiment of the present invention comprises polyoxyethylated castor oil aged according to the present invention, paclitaxel, and ethanol. Optionally, the pharmaceutical composition comprises 500–550 mg/mL of polyoxyethylated castor oil and 40–60% of ethanol vol/vol. For example, in a very particular embodiment, the pharmaceutical composition comprises 527 mg/mL of polyoxyethylated castor oil and 49.7% of ethanol vol/vol.

Pharmaceutical compositions according to the present invention are typically supplied as a nonaqueous solution intended for dilution with a suitable aqueous parenteral fluid prior to intravenous infusion. The pharmaceuticals are generally available in different sized single dose or multidose sealed vials. For example, 30 mg (5 ml), 100 mg (16.7 ml), and 300 mg (50 ml) vials of paclitaxel/Cremophor/ethanol are currently produced.

In order to administer the pharmaceutical compositions from these vials, the compositions are diluted with an aqueous solution so that intravenous infusions which typically have 135 to 175 mg/m$^2$ paclitaxel may be delivered over a period of 3 to 24 hours.

Aging the polyoxyethylated castor oil by exposing it to a gas comprising oxygen may be performed over a wide range of temperatures, pressures and times. For example, aging may optionally be performed at a temperature range between 0° C. and 70° C. Preferably, aging the polyoxyethylated castor oil is performed for at least 1 day, more preferably for at least 3 days, and most preferably for at least 7 days, at a temperature range between 30° C. and 70° C., more preferably between 40° C. and 60° C., and most preferably between 45° C. and 55° C.

Figure 2:
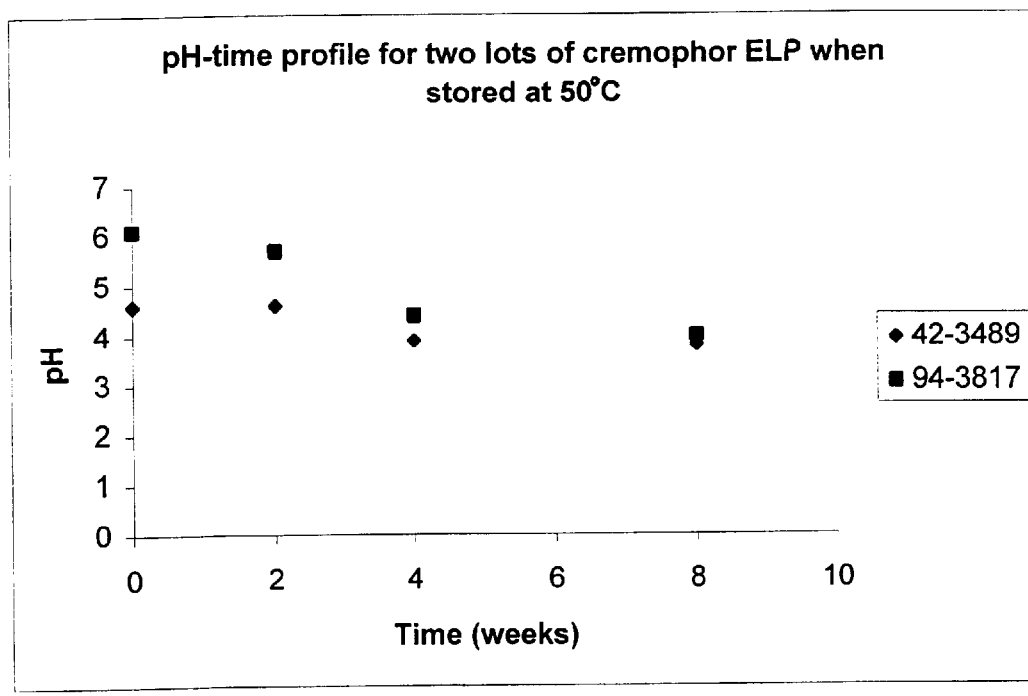
FIG. 2 is a plot over time of the pH of samples of Cremophor® ELP (after having been diluted 1/10(vol/vol) with $H_2O$) that have been stored at 50° C. at ambient atmospheric pressure.
Figure 3:
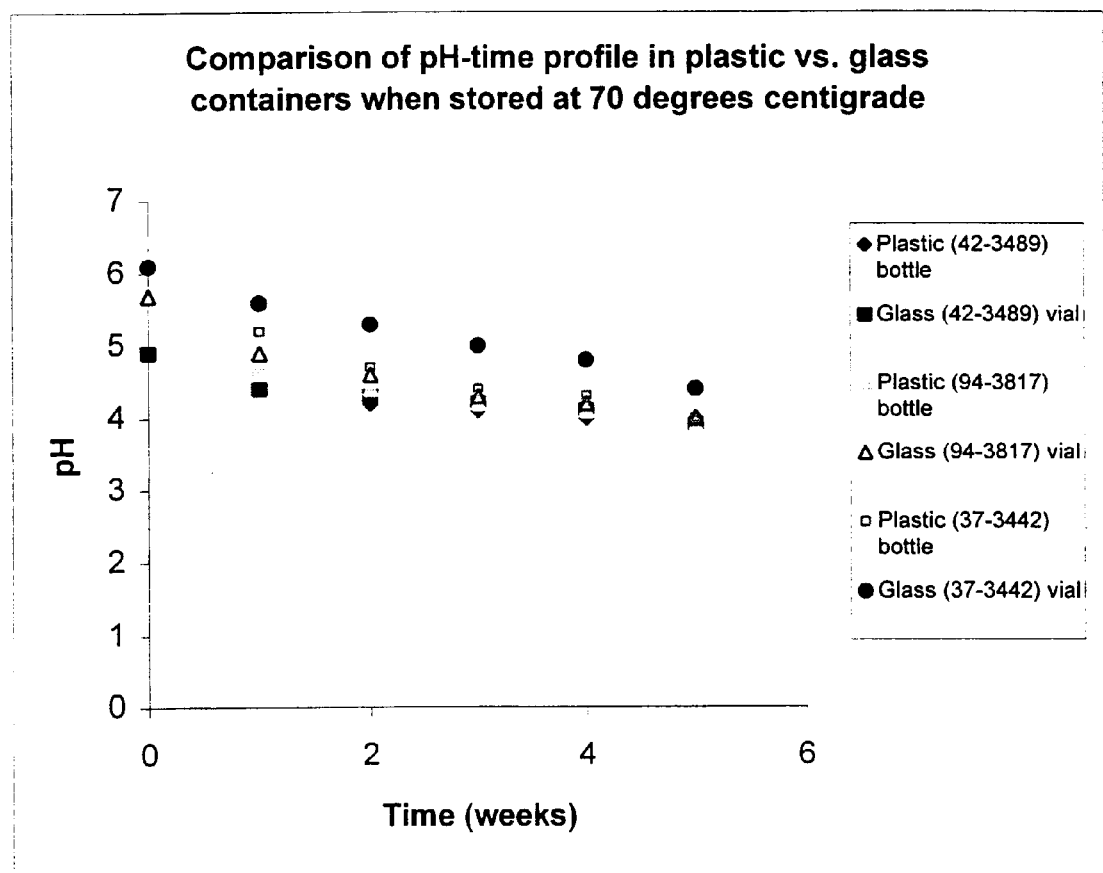
FIG. 3 is a plot over time of the pH of samples of Cremophor® ELP (after having been diluted 1/10(vol/vol) with $H_2O$) that have been stored at 70° C. at ambient atmospheric pressure.

As shown in Examples 1–3 herein and FIGS. 1–3, acidification of polyoxyethylated castor oil is accelerated with elevated temperatures, although the rate of acceleration appears to decrease at temperatures above 50° C. Nevertheless, aging polyoxyethylated castor oil at temperatures higher than 70° C. is still intended to fall within the scope of the present invention.

As described herein with regard to Example 4, sparging polyoxyethylated castor oil with air can be used to accelerate the acidification of polyoxyethylated castor oil. Sparging functions to agitate the polyoxyethylated castor oil. More importantly, sparging improves mixing between the sparged air and the polyoxyethylated castor oil.

One of skill in the art will also appreciate that increasing the pressure of an atmospheric gas mixture over the polyoxyethylated castor oil could accelerate the aging of the polyoxyethylated castor oil. Increasing the pressure could also allow higher temperatures to be used for incubating the polyoxyethylated castor oil. For example, aging the polyoxyethylated castor oil can be performed for at least 30 minutes at a temperature range between 0° C. and 70° C. by pressurizing the polyoxyethylated castor oil to be at least 1.2 atmospheric pressure, optionally at least 1.5 atmospheric pressure, optionally at least 2.0 atmospheric pressure, and optionally at least 3.0 atmospheric pressure.

Aging may be performed for a variety of periods of time. How long the polyoxyethylated castor oil needs to be aged is dependent upon the aging conditions, for example the temperature, the pressure, and how the polyoxyethylated castor oil is exposed to oxygen. As described herein with regard to Examples 1–3 and FIGS. 1–3, aging of polyoxyethylated castor oil can be accelerated when aging is performed at higher temperatures and/or with sparging. In one variation, aging is performed for at least 30 minutes, preferably for at least 1 day, more preferably for at least 3 days, and most preferably for at least 7 days.

It should be recognized that wide variations of temperature, pressure, and time condition(s), including conditions not exemplified herein, are intended within the scope of the instant invention, so long as a desired level of aging is achieved.

The acidity of polyoxyethylated castor oil can be readily monitored by monitoring the pH of a solution comprising a sample of the polyoxyethylated castor oil which has been diluted 1:10 with water. This allows the aging of the polyoxyethylated castor oil to be efficiently monitored. As a result, the aging process may be monitored and discontinued when the pH of the diluted solution reaches a desired pH. Accordingly, different aging conditions may be employed without losing track of the acidification of the polyoxyethylated castor oil.

When obtained from commercial suppliers, polyoxyethylated castor oil, prior to aging, typically has a pH greater than 6 when diluted with 1:10 with water. According to the present invention, the desired pH to which the polyoxyethylated castor oil should be aged is less than 5.9, optionally less than 5.5, optionally less than 5 and optionally less than 4.8. Optionally, the pH of the diluted solution of the aged polyoxyethylated castor oil may be between 3.7 and 5.9, 3.8 and 5.5, 3.9 and 5, or 4 and 4.8.

Sometimes, the commercially available polyoxyethylated castor oil, for example, Cremophor® ELP supplied by BASF, is within a pH range of 5.0–7.0. If the polyoxyethylated castor oil is at pH lower than 6 but higher than 5.0, it may also be aged according to the present invention to reach a pH equal to or lower than 4.9, optionally equal to or lower than 4.7, optionally equal to or lower than 4.5, and optionally equal to or lower than 4.2.

Optionally, aging the polyoxyethylated castor oil is performed until the aged polyoxyethylated castor oil, if diluted 1:10 in water, has a pH between 3.7 and 4.9, optionally between 3.8 and 4.5, optionally between 3.9 and 4.3, and optionally between 4.0 and 4.5.

The polyoxyethylated castor oil used in the pharmaceutical compositions of the present invention should be aged sufficiently so that the pharmaceutically active agent comprised in the pharmaceutical composition is stable. For example, in one variation, at least 80% of the potency of the pharmaceutically active agent is retained by the pharmaceutical composition after the pharmaceutical composition is stored for at least 7 days at 40° C. Preferably, at least 90%, 95% or more of the potency of the pharmaceutically active agent is retained. For the purposes of this application, storage for at least 7 days at 40° C. is used as a benchmark.

Optionally, the pharmaceutical composition may further comprise additional constituents including any additives that are appropriate for the intravenous administration route used for paclitaxel. Thus, any additive that is soluble, suspendable or emulsifiable in aged polyoxyethylated castor oil may be employed. Such additives may include microcrystalline and ground amorphous solids, in suspension, soluble solids and miscible liquids in solution, and emulsified immiscible liquids, typically with an emulsifying agent such as lecithin and surfactants including detergents.

Pharmaceutically acceptable alcohols may also be added to the pharmaceutical composition. For example, ethanol is commonly used in on combination with polyoxyethylated castor oil for the formulation of paclitaxel. Optionally, a pharmaceutically acceptable glycol such as propylene glycol and polyethylene glycol (PEG) or amide such as 2-pyrrolidone, N-methyl-pyrrolidone and N,N-dimethyl acetamide may be added to the aged polyoxyethylated castor oil or the pharmaceutical composition.

Antioxidants may also be added to the pharmaceutical composition. Antioxidants have previously been used to stabilize paclitaxel in pharmaceutical compositions for example as disclosed in U.S. Pat. Nos. 6,153,644 and 6,071,952 to Owens et al., and may be added to formulations according to the instant invention.

It is preferred that no agent is added that functions to increase the acidity of the polyoxyethylated castor oil.

However, a chemical acidifying agent may optionally be added to the polyoxyethylated castor oil before, during or after the aging process to further increase the acidity of the polyoxyethylated castor oil. The acidifying agent may be an organic acid. Examples of organic acid include, but are not limited to, ascorbic acid, citric acid, tartaric acid, lactic acid, oxalic acid, formic acid, benzene sulphonic acid, benzoic acid, maleic acid, glutamic acid, succinic acid, aspartic acid, diatrizoic acid, and acetic acid. The acidifying agent may also be an inorganic acid, such as hydrochloric acid, sulphuric acid, phosphoric acid, and nitric acid.

EXAMPLES

The following examples further illustrate the invention and are not to be construed to limit the claims in any manner.

Example 1

Three different lots of Cremophor® ELP were stored in original plastic containers under ambient conditions. Samples from these lots were taken at different times. The pH of these samples, after being diluted 1:10 with water, was measured. Table 1 provides the pH measurements for the samples. The pH measurements are also plotted in FIG. 1. As can be seen from both Table 1 and FIG. 1, Cremophor® ELP becomes more acidic over time. Without being bound by theory, it appears from FIG. 1 that the acidification of the Cremophor® ELP decelerates over time under ambient conditions such that the resulting pH may plateau around pH 3.6 and 4.0.

TABLE 1 pH of different lots of Cremophor ELP measured at predetermined time intervals.

| Lot # → | 14-3441 | 42-3489 | 94-3817 |
|---|---|---|---|
| pH on Certificate of Analysis provided by BASF→ | 6.4 | 6.1 | 6.1 |
| Time (Months)↓ | | | |
| Initial | 4.1 | 5.1 | 6.1 |
| 1 | 4.2 | 5.3 | 6.2 |
| 2 | 4.0 | 4.7 | 6.0 |
| 3 | 3.6 | 4.1 | 5.6 |
| 4 | 3.6 | 4.0 | 5.0 |

Example 2

Twenty (20) mL aliquots obtained from two lots of Cremophor® ELP were stored in glass vials at 50° C. Samples from these aliquots were taken at different times. The pH of these samples, after being diluted 1:10 with water, was measured. Table 2 provides the pH measurements for the samples. The pH measurements are also plotted in FIG. 2.

As can be seen from both the table and FIG. 2, increasing the storage temperature from ambient to 50° C. accelerates the rate at which the acidity of the Cremophor increases. For example, the pH of samples from Lot 94-3817 stored at 50° C. dropped from 6.1 to 4.4 in four weeks whereas it took samples from Lot 94-3817 stored at ambient conditions to drop from pH 6.1 to pH 5.0 in four months (see Table 1 for results).

TABLE 2 pH measurements of different lots of Cremophor ® ELP at predetermined time intervals following storage at 50° C.

| | 42-3489 | 94-3817 |
|---|---|---|
| pH on Certificate of Analysis provided by BASF→ | 6.1 | 6.1 |
| Time (weeks)↓ | | |
| Initial | 4.6 | 6.1 |
| 2 | 4.6 | 5.7 |
| 4 | 3.9 | 4.4 |
| 8 | 3.8 | 4.0 |

Example 3

Twenty (20) mL aliquots obtained from three lots of Cremophor® ELP were stored in glass vials and in plastic containers at 70° C. Samples from these aliquots were taken at different times. The pH of these samples, after being diluted 1:10 with water, was measured. Table 3 provides the pH measurements for the samples. The pH measurements are also plotted in FIG. 3.

Increasing the storage temperature from 50° C. to 70° C. does not greatly accelerate the rate at which the acidity of the Cremophor increases when results for different lots of Cremophor ELP in Table 2 are compared with corresponding results in Table 3.

The type of container used to age Cremophor® ELP did not appear to be critical. For example, the pH of samples from Lot 94-3817 stored at 70° C. dropped from pH 6.1 to 4.1 in four weeks in plastic container and pH 4.2 in the same time when stored in glass container. However, the pH data from Lot #37-3442 suggests some vulnerability of plastic to pH drop over glass and may be attributed to high permeability of plastic to air. A larger sample size may be required to confirm this observation. A strong linear relationship between pH drop and time over the entire range of pH 3.5 to 6.0 is not evidenced based on the $r^2$ values except for lot 37-3442 contained in a glass vial in which case the pH measurements were limited to the range of 6.1–4.4. It appears that due to deceleration in the pH drop around pH of 4, the slope beyond this point changes thereby deviating from linearity.

Lot #94-3817 and 37-3442 have similar slopes and differ from that of Lot #42-3489. Decrease in the slope in the latter case is probably due to deceleration in the pH drop beyond pH of 4.4.

TABLE 3

| Lot # → | 42-3489 | | 94-3817 | | 37-3442 | |
|---|---|---|---|---|---|---|
| pH on Certificate of Analysis provided by BASF→ | 6.1 | | 6.1 | | 6.8 | |
| Time (weeks)↓ | | | | | | |
| Initial | 4.9 | | 5.7 | | 6.1 | |
| Container Type→ | Plastic Bottle | Glass Vial | Plastic Bottle | Glass Vial | Plastic Bottle | Glass Vial |
| 1 | 4.4 | 4.4 | 4.7 | 4.9 | 5.2 | 5.6 |
| 2 | 4.2 | 4.3 | 4.4 | 4.6 | 4.7 | 5.3 |
| 3 | 4.1 | 4.2 | 4.2 | 4.3 | 4.4 | 5.0 |
| 4 | 4.0 | 4.1 | 4.1 | 4.2 | 4.3 | 4.8 |
| 5 | 3.9 | 3.9 | 3.9 | 4.0 | 4.0 | 4.4 |
| Slopes | −0.18 | −0.17 | −0.31 | −0.31 | −0.39 | −0.32 |
| $r^2$ | 0.86 | 0.89 | 0.82 | 0.89 | 0.89 | 0.98 |

Example 4

This experiment was performed in order to evaluate whether sparging with air affects the rate at which the polyoxyethylated castor oil acidifies. It is noted that this experiment was performed on larger volumes (4 L) than the volumes used in Examples 1–3.

A temperature controlled stainless steel jacketed vessel was charged twice, each time with 4 L of polyoxyethylated castor oil from the same lot, Lot #63-4693. While the first time, the vessel was fitted with an air sparger (flow rate of 4.65 Standard Liters Per Minute) and sparged with compressed air (treatment A); sparging was eliminated the second time (treatment B). In both treatment A and B the polyoxyethylated castor oil contained in the vessel was incubated at 50° C. to 60° C. No additional agitation was provided other than the agitation caused by sparging. The temperature of the polyoxyethylated castor oil was measured periodically.

Samples from the vessel were taken at different times during treatment A and B. The pH of these samples, after being diluted 1:10 with water, was measured. Table 4 provides the pH measurements for the samples. The experiment was conducted until samples from the vessel with sparging were found to have a pH between 4.0–4.8 The experiment was continued a few additional days in treatment B (without sparging) and was discontinued thereafter.

TABLE 4

| Day | Temperature of the contents (° C.) | Treatment A Sparged w/air pH 6.4 (BASF, Cert. of Analysis) | Treatment B Without air |
| --- | --- | --- | --- |
| 0 | — | 6.6 | 6.6 |
| 1 | 52 | 6.4 | 6.6 |
| 2 | 56 | 6.6 | 6.6 |
| 3 | — | 6.3 | 6.6 |
| 4 | 62 | 6.0 | — |
| 5 | — | — | — |
| 6 | — | — | 6.5 |
| 7 | 60 | 4.4 | 6.4 |
| 8 | — | — | 6.3 |
| 9 | — | — | 6.3 |
| 13 | — | — | 5.9 |

As can be seen from Table 4, air sparging was found to significantly accelerate the acidification of polyoxyethylated castor oil. For example, diluted samples of sparged polyoxyethylated castor oil had a pH of 4.4 after one week. Meanwhile, diluted samples of polyoxyethylated castor oil that was not sparged had a pH of 5.9 after 13 days.

The observed increased rate of acidification as a result of sparging may be due to mixing of the polyoxyethylated castor oil itself caused by sparging or mixing between the polyoxyethylated castor oil and sparged air.

The observation from Example 3 that acidification is faster in a more air permeable container (i.e., plastic) is consistent with sparging enhances the acidification kinetics by a combination of mixing and the delivery of air to the polyoxyethylated castor oil.

Example 5

8024 grams of Cremophor® ELP was aged in four separate containers (2006 g/container) at 50° C. at ambient pressure with sparging. Aging was performed in the temperature controlled stainless steel jacketed vessel, fitted with an air sparger (Flow rate of 4.65 Standard Liters Per Minute) used in Example 4. After aging for 7 days, the pH of a diluted sample of the polyoxyethylated castor oil was below 4.8 for all the containers, the pH measurements varying from 4.3 to 4.5 between the containers.

Example 6

8024 grams of Cremophor® ELP was aged in four separate containers (2006 g/container) at 60° C. at ambient pressure with sparging. Aging was performed in the temperature controlled stainless steel jacketed vessel, fitted with an air sparger (Flow rate of 4.65 Standard Liters Per Minute) used in Example 4. After aging for 7 days, the pH of a diluted sample of the polyoxyethylated castor oil was below 4.8 for all the containers, the pH measurements varying from 4.3 to 4.5 between the containers.

Example 7

A large batch of pharmaceutical compositions according to the present invention may be formed as follows. 750 grams of a polyoxyethylated castor oil aged according to the present invention may be placed into a 2 liter glass carboy. 560 grams of Dehydrated Ethanol, USP may then be added to the aged polyoxyethylated castor oil and mixed for a minimum of 10 minutes or until homogeneously dispersed. The headspace of the carboy is flushed with filtered nitrogen while mixing. Nitrogen flushing of the carboy headspace is continued as 8.5 grams of paclitaxel are added and mixed until completely dissolved. The final solution weight is adjusted to 1,325 grams with dehydrated ethanol, flushed with filtered nitrogen and mixed thoroughly. This final solution is aseptically filled into 5 ml unit vials.

While the instant invention is disclosed with reference to preferred embodiments detailed above, it is to be understood that these embodiments are intended in an illustrative or exemplary rather than in a limiting sense, as it is contemplated that modifications will readily occur to those skilled in the art, modifications which will be within the spirit of the invention and the scope of the appended claims. All patents, papers, articles, references and books cited herein are incorporated by reference in their entirety.

What is claimed is:

1. A method for preparing a pharmaceutical composition comprising:

taking polyoxyethylated castor oil which if diluted 1:10 in water has a pH greater than 6 and aging the polyoxyethylated castor oil by exposing the polyoxyethylated castor oil to a gas comprising oxygen for a period of time, the exposure to the gas over the period of time causing an acidity of the polyoxyethylated castor oil to increase; and forming a pharmaceutical composition comprising the aged polyoxyethylated castor oil and paclitaxel;

wherein at least 80% of the paclitaxel potency is retained by the pharmaceutical composition after the pharmaceutical composition is stored for at least 7 days at 40° C.

2. The method according to claim 1, further comprising adding an antioxidant to the aged polyoxyethylated castor oil.

3. The method according to claim 1, further comprising adding a pharmaceutically acceptable alcohol to the aged polyoxyethylated castor oil.

4. The method according to claim 3, wherein the pharmaceutically acceptable alcohol is ethanol.

5. The method according to claim 1, further comprising adding a pharmaceutically acceptable glycol to the aged polyoxyethylated castor oil.

6. The method according to claim 5, wherein the pharmaceutically acceptable glycol is propylene glycol or polyethylene glycol.

7. The method according to claim 1, further comprising adding an antioxidant to the pharmaceutical composition.

8. The method according to claim 7, wherein the antioxidant is vitamin E, vitamin C or their derivatives.

9. The method according to claim 7, further comprising adding a pharmaceutically acceptable alcohol to the aged polyoxyethylated castor oil.

10. The method according to claim 1, wherein aging the polyoxyethylated castor oil is performed for at least 30 minutes at a temperature range between 0° C. and 70° C.

11. The method according to claim 1, wherein aging the polyoxyethylated castor oil is performed for at least 30 minutes at a temperature range between 30° C. and 70° C.

12. The method according to claim 1, wherein aging the polyoxyethylated castor oil is performed for at least 30 minutes at a temperature range between 40° C. and 60° C.

13. The method according to claim 1, wherein aging the polyoxyethylated castor oil is performed for at least 7 days at a temperature range between 40° C. and 60° C.

14. The method according to claim 1, wherein aging the polyoxyethylated castor oil is performed for at least 30 minutes at a temperature range between 0° C. and 70° C. by sparging the polyoxyethylated castor oil with air.

15. The method according to claim 1, wherein aging the polyoxyethylated castor oil is performed for at least 30 minutes at a temperature range between 40° C. and 60° C. by sparging the polyoxyethylated castor oil with air.

16. The method according to claim 1, wherein aging the polyoxyethylated castor oil is performed for at least 30 minutes at a temperature range between 0° C. and 70° C. by pressurizing the polyoxyethylated castor oil to be at least 1.5 atmospheric pressure.

17. The method according to claim 1, wherein aging the polyoxyethylated castor oil is performed for at least 30 minutes at a temperature range between 0° C. and 70° C. by pressurizing the polyoxyethylated castor oil to be at least 1.5 atmospheric pressure.

18. The method according to claim 1, wherein at least 90% of the paclitaxel potency is retained by the pharmaceutical composition after the pharmaceutical composition is stored for at least 7 days at 40° C.

19. The method according to claim 1, wherein at least 95% of the paclitaxel potency is retained by the pharmaceutical composition after the pharmaceutical composition is stored for at least 7 days at 40° C.

20. The method according to claim 1, wherein the polyoxyethylated castor oil is selected from the group consisting of: Cremophor® EL and Cremophor® ELP.

21. A method for preparing a pharmaceutical composition of paclitaxel comprising:
    taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and
    forming a pharmaceutical composition comprising the aged polyoxyethylated castor oil and paclitaxel.

22. The method according to claim 21, wherein aging the polyoxyethylated castor oil is performed until the aged polyoxyethylated castor oil, if diluted 1:10 in water, has a pH less than or equal to 5.5.

23. The method according to claim 21, wherein aging the polyoxyethylated castor oil is performed until the aged polyoxyethylated castor oil, if diluted 1:10 in water, has a pH less than or equal to 5.

24. The method according to claim 21, wherein aging the polyoxyethylated castor oil is performed until the aged polyoxyethylated castor oil, if diluted 1:10 in water, has a pH equal to or less than 4.8.

25. The method according to claim 21, wherein aging the polyoxyethylated castor oil is performed until the aged polyoxyethylated castor oil, if diluted 1:10 in water, has a pH between 3.7 and 5.9.

26. The method according to claim 21, wherein aging the polyoxyethylated castor oil is performed until the aged polyoxyethylated castor oil, if diluted 1:10 in water, has a pH between 3.8 and 5.5.

27. The method according to claim 21, wherein aging the polyoxyethylated castor oil is performed until the aged polyoxyethylated castor oil, if diluted 1:10 in water, has a pH between 3.9 and 5.

28. The method according to claim 21, wherein aging the polyoxyethylated castor oil is performed until the aged polyoxyethylated castor oil, if diluted 1:10 in water, has a pH between 4 and 4.8.

29. The method according to claim 21, further comprising adding an antioxidant to the aged polyoxyethylated castor oil.

30. The method according to claim 21, further comprising adding a pharmaceutically acceptable alcohol to the aged polyoxyethylated castor oil.

31. The method according to claim 21, wherein aging the polyoxyethylated castor oil is performed for at least 30 minutes at a temperature range between 0 and 70° C.

32. The method according to claim 21, wherein at least 80% of the paclitaxel potency is retained by the pharmaceutical composition after the pharmaceutical composition is stored for at least 7 days at 40° C.

33. The method according to claim 21, wherein at least 90% of the paclitaxel potency is retained by the pharmaceutical composition after the pharmaceutical composition is stored for at least 7 days at 40° C.

34. The method according to claim 21, wherein at least 95% of the paclitaxel potency is retained by the pharmaceutical composition after the pharmaceutical composition is stored for at least 7 days at 40° C.

35. The method according to claim 21, wherein aging causes the pH of the polyoxyethylated castor oil, if diluted 1:10 in water, to decrease without requiring an agent to be added that functions to increase the acidity of the polyoxyethylated castor oil.

36. The method according to claim 21, wherein the polyoxyethylated castor oil is selected from the group consisting of: Cremophor® EL and Cremophor® ELP.

37. A method for preparing a pharmaceutical composition comprising:
    taking polyoxyethylated castor oil which if diluted 1:10 in water has a pH greater than 6 and aging the polyoxyethylated castor oil by exposing the polyoxyethylated castor oil to a gas comprising oxygen for a period of time, the exposure to the gas over the period of time causing an acidity of the polyoxyethylated castor oil to increase; and
    forming a pharmaceutical composition comprising the aged polyoxyethylated castor oil, ethanol and paclitaxel;
    wherein at least 80% of the paclitaxel potency is retained by the pharmaceutical composition after the pharmaceutical composition is stored for at least 7 days at 40° C.

38. The method according to claim 37, wherein at least 80% of the paclitaxel potency is retained by the pharmaceutical composition after the pharmaceutical composition is stored for at least 7 days at 40° C.

39. The method according to claim 37, wherein at least 90% of the paclitaxel potency is retained by the pharmaceutical composition after the pharmaceutical composition is stored for at least 7 days at 40° C.

40. The method according to claim 37, wherein at least 95% of the paclitaxel potency is retained by the pharmaceutical composition after the pharmaceutical composition is stored for at least 7 days at 40° C.

41. The method according to claim 37, wherein the pharmaceutical composition comprises 500–550 mg/mL of polyoxyethylated castor oil, and 40–60% of ethanol vol/vol.

42. The method according to claim 37, wherein the pharmaceutical composition comprises 527 mg/mL of polyoxyethylated castor oil, and 49.7% of ethanol vol/vol.

43. A method for preparing a pharmaceutical composition of paclitaxel comprising:

taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and forming a pharmaceutical composition comprising the aged polyoxyethylated castor oil, ethanol and paclitaxel;

wherein at least 80% of the paclitaxel potency is retained by the pharmaceutical composition after the pharmaceutical composition is stored for at least 7 days at 40° C.

44. The method according to claim 43, wherein aging the polyoxyethylated castor oil is performed until the aged polyoxyethylated castor oil, if diluted 1:10 in water, has a pH equal to or less than 4.7.

45. The method according to claim 43, wherein aging the polyoxyethylated castor oil is performed until the aged polyoxyethylated castor oil, if diluted 1:10 in water, has a pH between 3.7 and 4.9.

46. The method according to claim 43, wherein aging the polyoxyethylated castor oil is performed until the aged polyoxyethylated castor oil, if diluted 1:10 in water, has a pH between 3.9 and 4.3.

47. The method according to claim 43, wherein at least 90% of the paclitaxel potency is retained by the pharmaceutical composition after the pharmaceutical composition is stored for at least 7 days at 40° C.

48. The method according to claim 43, wherein at least 95% of the paclitaxel potency is retained by the pharmaceutical composition after the pharmaceutical composition is stored for at least 7 days at 40° C.

49. The method according to claim 43, wherein the pharmaceutical composition comprises 500–550 mg/mL of polyoxyethylated castor oil, and 40–60% of ethanol vol/vol.

50. The method according to claim 43, wherein the pharmaceutical composition comprises 527 mg/mL of polyoxyethylated castor oil, and 49.7% of ethanol vol/vol.

51. A pharmaceutical composition comprising:

polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and paclitaxel;

wherein the pharmaceutical composition does not comprise an agent added to the polyoxyethylated castor oil that functions to increase the acidity of the polyoxyethylated castor oil.

52. The pharmaceutical composition according to claim 51, wherein at least 80% of the paclitaxel potency is retained by the pharmaceutical composition after the pharmaceutical composition is stored for at least 7 days at 40° C.

53. The pharmaceutical composition according to claim 51, wherein at least 90% of the paclitaxel potency is retained by the pharmaceutical composition after the pharmaceutical composition is stored for at least 7 days at 40° C.

54. The pharmaceutical composition according to claim 51, wherein at least 95% of the paclitaxel potency is retained by the pharmaceutical composition after the pharmaceutical composition is stored for at least 7 days at 40° C.

55. The pharmaceutical composition according to claim 51, wherein the pharmaceutical composition further comprises ethanol.

56. The pharmaceutical composition according to claim 55, wherein the pharmaceutical composition comprises 500–550 mg/mL of polyoxyethylated castor oil, and 40–60% of ethanol vol/vol.

57. The pharmaceutical composition according to claim 55, wherein the pharmaceutical composition comprises 527 mg/mL of polyoxyethylated castor oil, and 49.7% of ethanol vol/vol.

58. A pharmaceutical composition comprising:

polyoxyethylated castor oil that has been modified by taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and paclitaxel;

wherein at least 80% of the paclitaxel potency is retained by the pharmaceutical composition after the pharmaceutical composition is stored for at least 7 days at 40° C.

59. The pharmaceutical composition according to claim 58, wherein at least 90% of the paclitaxel potency is retained by the pharmaceutical composition after the pharmaceutical composition is stored for at least 7 days at 40° C.

60. The pharmaceutical composition according to claim 58, wherein at least 95% of the paclitaxel potency is retained by the pharmaceutical composition after the pharmaceutical composition is stored for at least 7 days at 40° C.

61. The pharmaceutical composition according to claim 58, wherein the pharmaceutical composition further comprises ethanol.

62. The pharmaceutical composition according to claim 61, wherein the pharmaceutical composition comprises 500–550 mg/mL of polyoxyethylated castor oil, and 40–60% of ethanol vol/vol.

63. The pharmaceutical composition according to claim 61, wherein the pharmaceutical composition comprises 527 mg/mL of polyoxyethylated castor oil, and 49.7% of ethanol vol/vol.

64. The pharmaceutical according to claim 61, wherein the concentration of paclitaxel in the pharmaceutical composition is about 1–20 mg/g.

65. A pharmaceutical comprising:

a sealed vial comprising polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and paclitaxel;

wherein the pharmaceutical does not comprise an agent added to the polyoxyethylated castor oil that functions to increase the acidity of the polyoxyethylated castor oil.

66. The pharmaceutical according to claim 65, wherein the vial further comprises ethanol.

67. A pharmaceutical comprising:
   a sealed vial comprising
      polyoxyethylated castor oil that has been modified by taking polyoxyethylated castor oil which if diluted 1:10 in water has a pH greater than 6 and aging the polyoxyethylated castor oil by exposing the polyoxyethylated castor oil to a gas comprising oxygen until the aged polyoxyethylated castor oil, if diluted 1:10 in water, has a pH equal to or less than 5.9; and
      paclitaxel;
wherein at least 80% of the paclitaxel potency is retained by the pharmaceutical after the pharmaceutical is stored for at least 7 days at 40° C.

68. The pharmaceutical according to claim 67, wherein the vial further comprises ethanol.

69. A pharmaceutical comprising:
   a sealed vial comprising
      polyoxyethylated castor oil that has been modified by taking polyoxyethylated castor oil which if diluted 1:10 in water has a pH greater than 5 and aging the polyoxyethylated castor oil by exposing the polyoxyethylated castor oil to a gas comprising oxygen until the aged polyoxyethylated castor oil, if diluted 1:10 in water, has a pH equal to or less than 4.9; and
      paclitaxel;
wherein at least 80% of the paclitaxel potency is retained by the pharmaceutical after the pharmaceutical is stored for at least 7 days at 40° C.

70. The pharmaceutical according to claim 69, wherein the vial further comprises ethanol.

* * * * *